(12) United States Patent
Du et al.

(10) Patent No.: US 9,884,823 B2
(45) Date of Patent: Feb. 6, 2018

(54) OXIME ETHER ACETATE COMPOUND, PREPARATION METHOD THEREFOR AND WEEDING APPLICATION THEREOF

(71) Applicant: ZHEJIANG UNIVERSITY OF TECHNOLOGY, Hangzhou, Zhejiang Province (CN)

(72) Inventors: Xiaohua Du, Hangzhou (CN); Dajie Mao, Hangzhou (CN); Zhenyuan Xu, Hangzhou (CN)

(73) Assignee: ZHEJIANG UNIVERSITY OF TECHNOLOGY, Hangzhou (CN)

( * ) Notice: Subject to any disclaimer, the term of this patent is extended or adjusted under 35 U.S.C. 154(b) by 0 days.

(21) Appl. No.: 15/125,540

(22) PCT Filed: Feb. 13, 2015

(86) PCT No.: PCT/CN2015/072976
§ 371 (c)(1),
(2) Date: Sep. 12, 2016

(87) PCT Pub. No.: WO2015/135413
PCT Pub. Date: Sep. 17, 2015

(65) Prior Publication Data
US 2017/0001961 A1     Jan. 5, 2017

(30) Foreign Application Priority Data

Mar. 11, 2014 (CN) .......................... 2014 1 0088191
Sep. 5, 2014 (CN) .......................... 2014 1 0452170

(51) Int. Cl.
| C07D 213/61 | (2006.01) |
| C07D 213/64 | (2006.01) |
| C07D 213/65 | (2006.01) |
| C07D 213/85 | (2006.01) |
| A01N 43/40  | (2006.01) |

(Continued)

(52) U.S. Cl.
CPC ........... *C07D 213/55* (2013.01); *A01N 43/40* (2013.01); *C07D 213/30* (2013.01); *C07D 213/57* (2013.01); *C07D 213/61* (2013.01); *C07D 213/64* (2013.01); *C07D 213/65* (2013.01);

(Continued)

(58) Field of Classification Search
None
See application file for complete search history.

(56) References Cited

U.S. PATENT DOCUMENTS 5,145,980 A    9/1992   Wenderoth et al.

FOREIGN PATENT DOCUMENTS

CN        1306506 A      8/2001

*Primary Examiner* — Alton Pryor
(74) *Attorney, Agent, or Firm* — Jiwen Chen

(57) ABSTRACT

The present invention discloses an oxime ether acetate compound containing a phenylpyridine moiety of formula (I), whose preparation method is as follows: (1) mixing a compound of formula (IV), a compound of formula (V), an alkaline substance A, a palladium catalyst and a solvent A; subjecting the mixture to a reaction at the temperature ranging from −10° C. to the reflux temperature for 0.5-20 hours to obtain a reaction solution A; post-treating the solution A to obtain a compound of formula (II); (2) mixing the compound of formula (II), an alkaline substance B, a phase transfer catalyst and a solvent B; subjecting the mixture to a reaction at the temperature ranging from −10° C. to the reflux temperature for 0.1-2 hours; then adding a compound of formula (III), continuing to react at the temperature ranging from −10° C. to the reflux temperature for 0.5-20 hours to obtain a reaction solution B; and post-treating the solution B to obtain the compound of formula (I). The oxime ether acetate compound containing a phenylpyridine moiety of formula (I) can be used for weeding in crops.

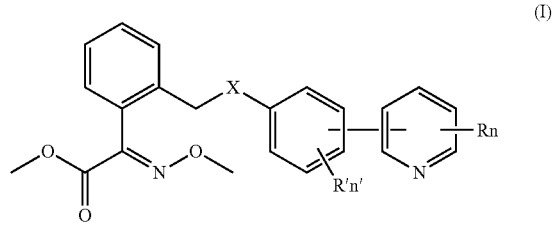

(I)

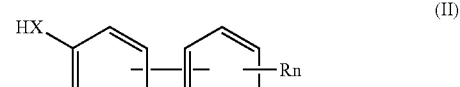

(II)

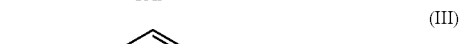

(III)

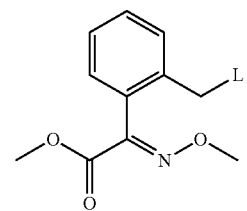

(IV)

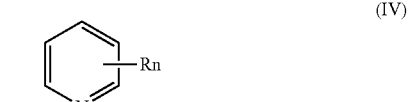

(V)

(Continued)

11 Claims, No Drawings

(51) Int. Cl.
    *C07D 213/55*     (2006.01)
    *C07D 213/84*     (2006.01)
    *C07D 213/30*     (2006.01)
    *C07D 213/57*     (2006.01)
    *C07D 213/76*     (2006.01)

(52) U.S. Cl.
    CPC ......... *C07D 213/76* (2013.01); *C07D 213/84* (2013.01); *C07D 213/85* (2013.01)

OXIME ETHER ACETATE COMPOUND, PREPARATION METHOD THEREFOR AND WEEDING APPLICATION THEREOF

This is a U.S. national stage application of PCT Application No. PCT/CN2015/072976 under 35 U.S.C. 371, filed Feb. 13, 2015 in Chinese, claiming the priority of Chinese Application No. 201410088191.1, filed Mar. 11, 2014 and Chinese Application No. 201410452170.3, filed Sep. 5, 2014, which are hereby incorporated by reference.

FIELD OF THE INVENTION

The present invention relates to oxime ether acetate compounds, and in particular, to oxime ether acetate compounds containing phenylpyridine moieties, preparation method therefor and use thereof as an active ingredient in controlling weeds in crops.

BACKGROUND TECHNOLOGY

Strobilurin fungicides, as a type of highly effective, broad-spectrum, low-toxicity fungicides, have been well developed and applied widely. Oxime ether acetate compounds are a very important type of strobilurins. But till now, the herbicidal activity of oxime ether acetate compounds has been rarely reported.

SUMMARY OF THE INVENTION

An object of the present invention is to provide oxime ether acetate compounds containing a phenylpyridine moieties that can be used to effectively control noxious weeds at a low dose, preparation method thereof and use thereof in weeding.

To achieve the above object, the present invention adopts the following technical solutions:

An oxime ether acetate compound containing a phenylpyridine moiety, having formula (I):

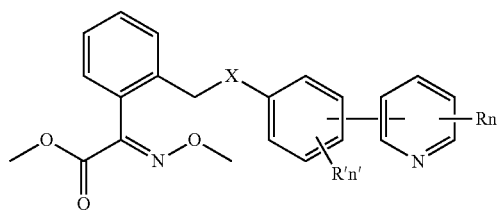

(I)

wherein, X is O, S, COO or NH;
R and n represent a substituent on the pyridine ring and the number of substituents respectively, wherein $0 \leq n \leq 4$, preferably, $0 \leq n \leq 3$, and n is a natural number, when n=0, it means that the pyridine ring does not contain R, when $0 < n \leq 4$, each of the substituents on the pyridine ring (i.e. R) is selected from the group consisting of $CH_3$, $OCH_3$, Br, Cl, F, CN, $CF_3$, $NO_2$ and OH, and the substituents (i.e. R) on the pyridine ring are same or different;
R' and n' represent a substituent on the benzene ring and the number of substituents, wherein $0 \leq n' \leq 4$, preferably, $0 \leq n' \leq 3$, and n' is a natural number, when n'=0, it means that the benzene ring does not contain R', when $0 < n' \leq 4$, each of the substituents on the pyridine ring (i.e. R') independent from each other is selected from the group consisting of $CH_3$, $OCH_3$, Br, Cl, F, CN, $CF_3$, $NO_2$ and OH, and the substituents (i.e. R') on the benzene ring are same or different;

relative to the benzene ring, pyridinyl is positioned at ortho-, meta- or para-position of X on the benzene ring, and relative to the pyridine ring, the substituted phenyl is positioned at ortho-, meta- or para-position of N on the pyridine ring.

In formula (I), the pyridine ring and the benzene ring can be linked in 9 ways, which is shown as formula (I-1)-formula (I-9).

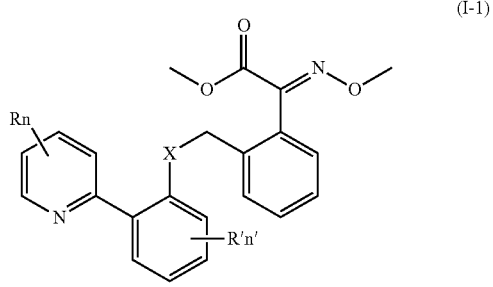

(I-1)

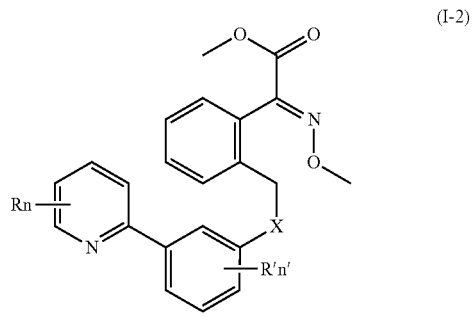

(I-2)

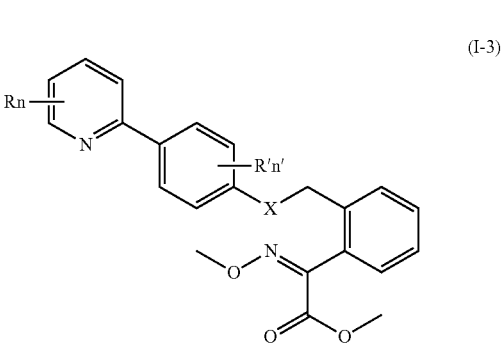

(I-3)

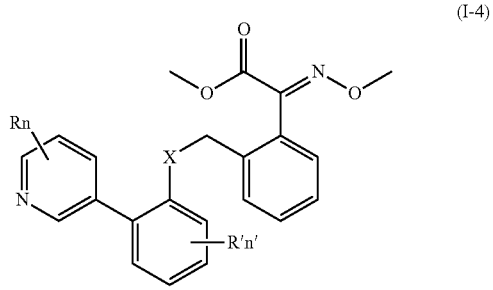

(I-4)

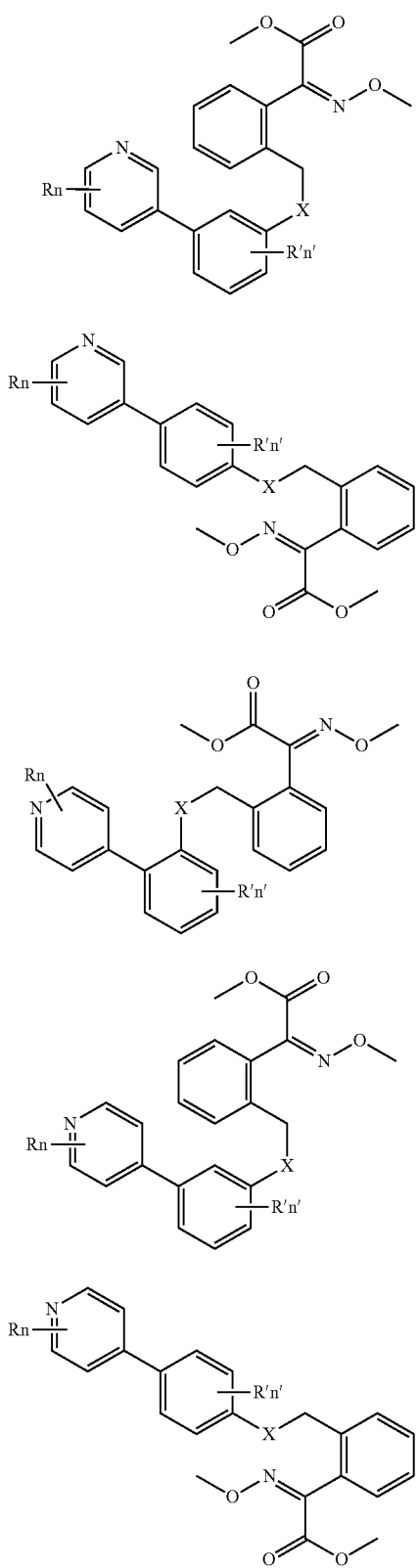

Wherein, in formula (I-1)~formula (I-3), relative to the phenyl ring, the pyridinyl group is positioned at ortho-, meta-, para-position of X on the benzene ring respectively; and relative to the pyridine ring, the substituted phenyl group is positioned at ortho-position of N on the pyridine ring;

in formula (I-4)~formula (I-6), relative to the phenyl ring, the pyridinyl group is positioned at ortho-, meta-, para-position of X on the benzene ring respectively; and relative to the pyridine ring, the substituted phenyl group is positioned at meta-position of N on the pyridine ring;

In formula (I-7)~formula (I-9), relative to the phenyl ring, the pyridinyl group is positioned at ortho-, meta-, para-position of X on the benzene ring respectively; and relative to the pyridine ring, the substituted phenyl group is positioned at para-position of N on the pyridine ring.

Preferably, the oxime ether acetate compound in the present invention has formula (I) wherein X is O.

More preferably, the oxime ether acetate compound in the present invention has formula (I) wherein X is O,
R is selected from the group consisting of Br, Cl, F, CN, $CF_3$ and $NO_2$; when $0<n\leq4$, the substituents (R) on the pyridine ring are same,
R' on the benzene ring is selected from the group consisting of Br, Cl, F, CN, $CF_3$ and $NO_2$, when $0<n'\leq4$, the substituents (R') on the benzene ring are same,
relative to the pyridine ring, the substituted phenyl group is positioned at ortho-, meta- or para-position of N on the pyridine ring, and relative to the benzene ring, the pyridinyl group is positioned at meta-position of X on the benzene ring.

Furthermore, preferably, the oxime ether acetate compound in the present invention has formula (I) wherein X is O,
R is selected from Br, Cl, F, CN, $CF_3$ or $NO_2$; when $0<n\leq4$, the substituents (R) on the pyridine ring are same,
R' on the benzene ring is selected from Br, Cl, F, CN, $CF_3$ or $NO_2$, when $0<n'\leq4$, the substituents (R') on the benzene ring is same, and
relative to the pyridine ring, the substituted phenyl group is positioned at ortho-position of N on the pyridine ring, and relative to the benzene ring, pyridinyl is positioned at meta-position of X on the benzene ring.

TABLE 1

List of synthesized compounds

| No. of Compound | linking position of substituted phenyl and pyridine ring | X (linking position of X and benzene ring) | Rn | R'n' |
|---|---|---|---|---|
| 1 | 2 | O(2-) | | |
| 2 | 3 | O(2-) | | |
| 3 | 4 | O(2-) | | |
| 4 | 2 | O(3-) | | |
| 5 | 3 | O(3-) | | |
| 6 | 4 | O(3-) | | |
| 7 | 2 | O(4-) | | |
| 8 | 3 | O(4-) | | |
| 9 | 4 | O(4-) | | |
| 10 | 2 | O(2-) | | 5-Cl |
| 11 | 2 | O(2-) | | 5-F |
| 12 | 2 | O(2-) | | 5-Br |
| 13 | 2 | O(2-) | | 5-CN |
| 14 | 2 | O(2-) | | 5-$NO_2$ |
| 15 | 2 | O(2-) | | 5-$CF_3$ |
| 16 | 2 | O(2-) | | 5-$CH_3$ |
| 17 | 2 | O(2-) | | 5-$OCH_3$ |
| 18 | 2 | O(2-) | | 3-OH |
| 19 | 2 | O(3-) | | 5-Cl |
| 20 | 2 | O(3-) | | 5-F |
| 21 | 2 | O(3-) | | 5-Br |
| 22 | 2 | O(3-) | | 5-CN |

TABLE 1-continued

List of synthesized compounds

| No. of Compound | linking position of substituted phenyl and pyridine ring | X (linking position of X and benzene ring) | Rn | R'n' |
|---|---|---|---|---|
| 23 | 2 | O(3-) | 5-NO$_2$ | |
| 24 | 2 | O(3-) | 5-CF$_3$ | |
| 25 | 2 | O(3-) | 5-CH$_3$ | |
| 26 | 2 | O(3-) | 5-OCH$_3$ | |
| 27 | 2 | O(4-) | 5-Cl | |
| 28 | 2 | O(4-) | 5-F | |
| 29 | 2 | O(4-) | 5-Br | |
| 30 | 2 | O(4-) | 5-CN | |
| 31 | 2 | O(4-) | 5-NO$_2$ | |
| 32 | 2 | O(4-) | 5-CF$_3$ | |
| 33 | 2 | O(4-) | 5-CH$_3$ | |
| 34 | 2 | O(4-) | 5-OCH$_3$ | |
| 35 | 3 | O(2-) | 5-Cl | |
| 36 | 3 | O(2-) | 5-F | |
| 37 | 3 | O(2-) | 5-Br | |
| 38 | 3 | O(2-) | 5-CN | |
| 39 | 3 | O(2-) | 5-NO$_2$ | |
| 40 | 3 | O(2-) | 5-CF$_3$ | |
| 41 | 3 | O(2-) | 5-CH$_3$ | |
| 42 | 3 | O(2-) | 5-OCH$_3$ | |
| 43 | 3 | O(3-) | 5-Cl | |
| 44 | 3 | O(3-) | 5-F | |
| 45 | 3 | O(3-) | 5-Br | |
| 46 | 3 | O(3-) | 5-CN | |
| 47 | 3 | O(3-) | 5-NO$_2$ | |
| 48 | 3 | O(3-) | 5-CF$_3$ | |
| 49 | 3 | O(3-) | 5-CH$_3$ | |
| 50 | 3 | O(3-) | 5-OCH$_3$ | |
| 51 | 3 | O(4-) | 5-Cl | |
| 52 | 3 | O(4-) | 5-F | |
| 53 | 3 | O(4-) | 5-Br | |
| 54 | 3 | O(4-) | 5-CN | |
| 55 | 3 | O(4-) | 5-NO$_2$ | |
| 56 | 3 | O(4-) | 5-CF$_3$ | |
| 57 | 3 | O(4-) | 5-CH$_3$ | |
| 58 | 3 | O(4-) | 5-OCH$_3$ | |
| 59 | 4 | O(2-) | 2-Cl | |
| 60 | 4 | O(2-) | 2-F | |
| 61 | 4 | O(2-) | 2-Br | |
| 62 | 4 | O(2-) | 2-CN | |
| 63 | 4 | O(2-) | 2-NO$_2$ | |
| 64 | 4 | O(2-) | 2-CF$_3$ | |
| 65 | 4 | O(2-) | 2-CH$_3$ | |
| 66 | 4 | O(2-) | 2-OCH$_3$ | |
| 67 | 4 | O(3-) | 2-Cl | |
| 68 | 4 | O(3-) | 2-F | |
| 69 | 4 | O(3-) | 2-Br | |
| 70 | 4 | O(3-) | 2-CN | |
| 71 | 4 | O(3-) | 2-NO$_2$ | |
| 72 | 4 | O(3-) | 2-CF$_3$ | |
| 73 | 4 | O(3-) | 2-CH$_3$ | |
| 74 | 4 | O(3-) | 2-OCH$_3$ | |
| 75 | 4 | O(4-) | 2-Cl | |
| 76 | 4 | O(4-) | 2-F | |
| 77 | 4 | O(4-) | 2-Br | |
| 78 | 4 | O(4-) | 2-CN | |
| 79 | 4 | O(4-) | 2-NO$_2$ | |
| 80 | 4 | O(4-) | 2-CF$_3$ | |
| 81 | 4 | O(4-) | 2-CH$_3$ | |
| 82 | 4 | O(4-) | 2-OCH$_3$ | |
| 83 | 2 | O(3-) | 3-CH$_3$ | |
| 84 | 2 | O(3-) | 4-CH$_3$ | |
| 85 | 2 | O(3-) | 6-CH$_3$ | |
| 86 | 2 | O(3-) | 3-CF$_3$ | |
| 87 | 2 | O(3-) | 4-CF$_3$ | |
| 88 | 2 | O(3-) | 6-CF$_3$ | |
| 89 | 2 | O(3-) | 3-NO$_2$ | |
| 90 | 2 | O(3-) | 4-NO$_2$ | |
| 91 | 2 | O(3-) | 6-NO$_2$ | |
| 92 | 2 | O(3-) | 3-Cl | |
| 93 | 2 | O(3-) | 4-Cl | |
| 94 | 2 | O(3-) | 6-Cl | |
| 95 | 2 | O(3-) | 3-CN | |
| 96 | 2 | O(3-) | 4-CN | |
| 97 | 2 | O(3-) | 6-CN | |
| 98 | 2 | O(3-) | 3,5-Cl,Cl | |
| 99 | 2 | O(3-) | 3,5,6-Cl,Cl,Cl | |
| 100 | 2 | O(3-) | 5,6-Cl,Cl | |
| 101 | 2 | O(3-) | 3-Cl, 5-CF$_3$ | |
| 102 | 2 | O(3-) | 3-Cl, 5-NO$_2$ | |
| 103 | 2 | O(3-) | 3-NO$_2$, 5-Cl | |
| 104 | 2 | O(3-) | 3-NO$_2$, 5-Br | |
| 105 | 2 | O(3-) | 3-NO$_2$, 6-Cl | |
| 106 | 2 | O(3-) | 3-NO$_2$, 6-Br | |
| 107 | 2 | O(3-) | 3-CN, 4-CH$_3$, 6-Cl | |
| 108 | 2 | O(3-) | 6-COOEt | |
| 109 | 3 | O(3-) | 2-Cl, 5-NO$_2$ | |
| 110 | 4 | O(3-) | 3,5-Cl,Cl | |
| 111 | 2 | O(3-) | | 4-Cl |
| 112 | 2 | O(3-) | | 4-CF$_3$ |
| 113 | 2 | O(3-) | | 4-NO$_2$ |
| 114 | 2 | O(3-) | | 4-CN |
| 115 | 2 | O(3-) | | 4-CH$_3$ |
| 116 | 2 | O(3-) | | 2,6-F,F |
| 117 | 2 | NH(3-) | | |
| 118 | 2 | O(4-) | 3-CH$_3$ | |
| 119 | 2 | O(4-) | 4-CH$_3$ | |
| 120 | 2 | O(4-) | 6-CH$_3$ | |
| 121 | 2 | O(4-) | 3-CF$_3$ | |
| 122 | 2 | O(4-) | 4-CF$_3$ | |
| 123 | 2 | O(4-) | 6-CF$_3$ | |
| 124 | 2 | O(4-) | 3-NO$_2$ | |
| 125 | 2 | O(4-) | 4-NO$_2$ | |
| 126 | 2 | O(4-) | 6-NO$_2$ | |
| 127 | 2 | O(4-) | 3-Cl | |
| 128 | 2 | O(4-) | 4-Cl | |
| 129 | 2 | O(4-) | 6-Cl | |
| 130 | 2 | O(4-) | 3-CN | |
| 131 | 2 | O(4-) | 4-CN | |
| 132 | 2 | O(4-) | 6-CN | |
| 133 | 2 | O(4-) | 3,5-Cl,Cl | |
| 134 | 2 | O(4-) | 3,5,6-Cl,Cl,Cl | |
| 135 | 2 | O(4-) | 5,6-Cl,Cl | |
| 136 | 2 | O(4-) | 3-Cl, 5-CF$_3$ | |
| 137 | 2 | O(4-) | 3-Cl, 5-NO$_2$ | |
| 138 | 2 | O(4-) | 3-NO$_2$, 5-Cl | |
| 139 | 2 | O(4-) | 3-NO$_2$, 5-Br | |
| 140 | 2 | O(4-) | 3-NO$_2$, 6-Cl | |
| 141 | 2 | O(4-) | 3-NO$_2$, 6-Br | |
| 142 | 2 | O(4-) | 3-CN, 4-CH$_3$, 6-Cl | |
| 143 | 2 | O(4-) | 6-COOEt | |
| 144 | 2 | O(4-) | 2-Cl, 5-NO$_2$ | |
| 145 | 2 | O(4-) | 3,5-Cl,Cl | |
| 146 | 2 | O(4-) | | 4-Cl |
| 147 | 2 | O(4-) | | 4-CF$_3$ |
| 148 | 2 | O(4-) | | 4-NO$_2$ |
| 149 | 2 | O(4-) | | 4-CN |
| 150 | 2 | O(4-) | | 4-CH$_3$ |
| 151 | 2 | O(4-) | | 2,6-F,F |
| 152 | 2 | NH(4-) | | |
| 153 | 2 | O(2-) | 3-CH$_3$ | |
| 154 | 2 | O(2-) | 4-CH$_3$ | |
| 155 | 2 | O(2-) | 6-CH$_3$ | |
| 156 | 2 | O(2-) | 3-CF$_3$ | |
| 157 | 2 | O(2-) | 4-CF$_3$ | |
| 158 | 2 | O(2-) | 6-CF$_3$ | |
| 159 | 2 | O(2-) | 3-NO$_2$ | |
| 160 | 2 | O(2-) | 4-NO$_2$ | |
| 161 | 2 | O(2-) | 6-NO$_2$ | |
| 162 | 2 | O(2-) | 3-Cl | |
| 163 | 2 | O(2-) | 4-Cl | |
| 164 | 2 | O(2-) | 6-Cl | |
| 165 | 2 | O(2-) | 3-CN | |
| 166 | 2 | O(2-) | 4-CN | |
| 167 | 2 | O(2-) | 6-CN | |
| 168 | 2 | O(2-) | 3,5-Cl,Cl | |

TABLE 1-continued

List of synthesized compounds

| No. of Compound | linking position of substituted phenyl and pyridine ring | X (linking position of X and benzene ring) | Rn | R'n' |
|---|---|---|---|---|
| 169 | 2 | O(2-) | 3,5,6-Cl,Cl,Cl | |
| 170 | 2 | O(2-) | 5,6-Cl,Cl | |
| 171 | 2 | O(2-) | 3-Cl, 5-CF$_3$ | |
| 172 | 2 | O(2-) | 3-Cl, 5-NO$_2$ | |
| 173 | 2 | O(2-) | 3-NO$_2$, 5-Cl | |
| 174 | 2 | O(2-) | 3-NO$_2$, 5-Br | |
| 175 | 2 | O(2-) | 3-NO$_2$, 6-Cl | |
| 176 | 2 | O(2-) | 3-NO$_2$, 6-Br | |
| 177 | 2 | O(2-) | 3-CN, 4-CH$_3$, 6-Cl | |
| 178 | 2 | O(2-) | 6-COOEt | |
| 179 | 2 | O(2-) | 2-Cl, 5-NO$_2$ | |
| 180 | 2 | O(2-) | 3,5-Cl,Cl | |
| 181 | 2 | O(2-) | | 4-Cl |
| 182 | 2 | O(2-) | | 4-CF$_3$ |
| 183 | 2 | O(2-) | | 4-NO$_2$ |
| 184 | 2 | O(2-) | | 4-CN |
| 185 | 2 | O(2-) | | 4-CH$_3$ |
| 186 | 2 | O(2-) | | 2,6-F,F |
| 187 | 2 | NH(2-) | | |

Note:
In Table 1, the numbering rules of benzene ring and pyridine ring are as follows: on the pyridine ring, the position of N is numbered as No. 1 position, and number the other positions according to the sequence which makes the position of substituted phenyl have the smallest number; and on the benzene ring, the position of pyridinyl is numbered as No. 1 position, then number the other positions according to the sequence which makes the position of X have the smallest number.

The present invention also provides a method for preparing the oxime ether acetate compound containing a phenylpyridine moiety, which comprises the following steps:

(1) Preparation of a compound of formula (II) (as shown in scheme 2: Mixing a compound of formula (IV), a compound of formula (V), an alkaline substance A, a palladium catalyst and a solvent A; subjecting the mixture to a reaction at the temperature ranging from −10° C. to the reflux temperature for 0.5-20 hours to obtain a reaction solution A; post-treating the solution A to obtain a compound of formula (II); in which the alkaline substance A is selected from the group consisting of potassium carbonate, potassium phosphate, potassium hydroxide, potassium t-butoxide and cesium fluoride; the palladium catalyst is selected from the group consisting of palladium chloride, palladium acetate, tetrakis (triphenyl phosphine) palladium, palladium triphenylphosphine acetate and [1,1'-bis (diphenylphosphino) ferrocene] dichloropalladium; the solvent A is selected from the group consisting of isopropyl alcohol, ethylene glycol, glycerol, ethanol, water, tetrahydrofuran, dioxane, toluene, xylene, PEG2000, and any combination thereof;

(2) Preparation of the compound of formula (I) (as shown in scheme 1): Mixing the obtained compound of formula (II), an alkaline substance B, a phase transfer catalyst and a solvent B; subjecting the mixture to a reaction at the temperature ranging from −10° C. to the reflux temperature for 0.1-2 hours; then adding a compound of formula (III), continuing to react at the temperature ranging from −10° C. to the reflux temperature for 0.5-20 hours to obtain a reaction solution B; and post-treating the solution B to obtain the compound of formula (I); in which, the alkaline substance B is selected from the group consisting of sodium hydride, sodium methoxide, tert-butyllithium, sodium hydroxide, potassium hydroxide, potassium carbonate and sodium carbonate; the phase transfer catalyst is selected from the group consisting of n-butyl ammonium bromide and 18-crown-6; and the solvent B is selected from the group consisting of N,N-dimethylformamide; N,N-dimethylacetamide; tetrahydrofuran, acetonitrile, acetone, methylene chloride, dimethyl sulfoxide, and any combination thereof.

In preparation step (1) of the present invention, it is recommended that, the mole ratio of the compound of formula (IV) to the compound of formula (V) ranges from 1:1 to 1:2, the mole ratio of the compound of formula (IV) to the alkaline substance A ranges from 1:2 to 1:3, the mole ratio of the compound of formula (IV) to the palladium catalyst ranges from 1:0.01 to 1:0.2; and the ration of the solvent A to the compound of formula (IV) ranges from 20 mL/g to 70 mL/g.

The reaction solution A is post-treated as follows: after completion of the reaction, the solvent is removed from the solution A by distillation under reduced pressure, then water is added to the residue, the mixture is extracted with ethyl acetate, the organic phase is dried with anhydrous magnesium sulfate, then filtered, and the filtrate is concentrated and dried to obtain the compound of formula (II).

In preparation step (2) of the present invention, it is recommended that, the mole ratio of the compound of formula (II) to the compound of formula (III) ranges from 1:1 to 1:2, the mole ratio of the compound of formula (II) to the alkaline substance B ranges from 1:1 to 1:3, the mole ratio of the compound of formula (II) to the phase transfer catalyst ranges from 1:0.01 to 1:0.2; and the ratio of the solvent B to the compound of formula (II) ranges from 20 mL/g to 30 mL/g.

The reaction solution B is post-treated as follows: after completion of the reaction, water and ethyl acetate are added into the reaction B for extraction, the combined ethyl acetate phase is reversely extracted by saturated brine, then the aqueous phase is discarded, the organic phase is dried, filtered and desolventized; then the resultant concentrate is subjected to silica gel column chromatography; use the petroleum ether/acetone mixed solvent with a volume ratio ranging from 1:1 to 30:1 as the eluent, the eluate containing the target compound is collected, concentrated and dried to obtain the compound of formula (I).

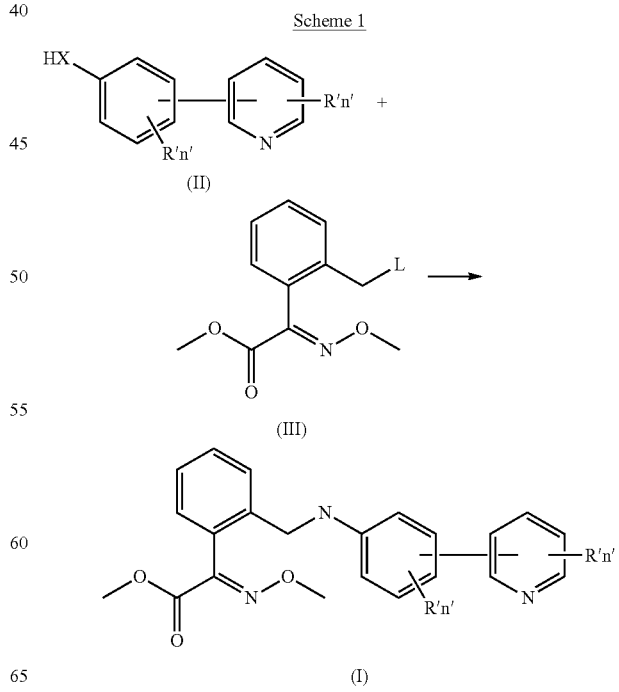

Scheme 2

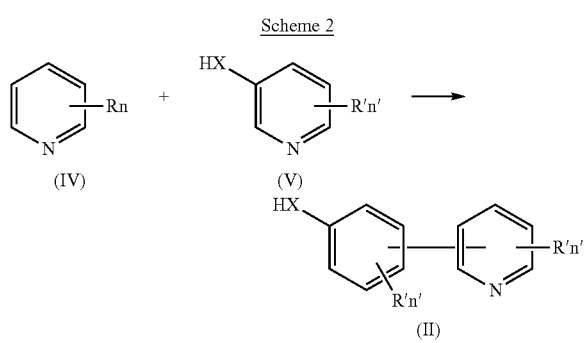

In the formula (III), L represents a leaving group and is Cl or Br. The compound of formula (III) can be prepared according to the method in prior art (refer to DE10017724, CN1793115A, CN101941921A, CN100357263C). In the formula (II), (IV) or (V), R and n represent a substituent on the pyridine ring and the number of substituents respectively, wherein 0≤n≤4, preferably, 0≤n≤3, and n is a natural number, when n=0, it means that the pyridine ring does not contain R, when 0<n≤4, each of the substituents on the pyridine ring independent from each other is selected from $CH_3$, $OCH_3$, Br, Cl, F, CN, $CF_3$, $NO_2$ or OH, and the substituents on the pyridine ring are same or different; R' and n' represent a substituent on the benzene ring and the number of substituents, wherein 0≤n'≤4, preferably, 0≤n'≤3, and n' is a natural number, when n'=0, it means that the benzene ring does not contain R', when 0<n'≤4, each of the substituents on the pyridine ring independent from each other is selected from $CH_3$, $OCH_3$, Br, Cl, F, CN, $CF_3$, $NO_2$ or OH, and the substituents on the benzene ring are same or different. In the formula (II) or (V), X is O, S, COO or NH. In the formula (II), relative to the benzene ring, pyridinyl is positioned at ortho-, meta- or para-position of XH on the benzene ring, and relative to the pyridine ring, the substituted phenyl is positioned at ortho-, meta- or para-position of N on the pyridine ring.

The letter A in the alkaline substance A, solvent A, and reaction solution A, and the letter B in the alkaline substance B, solvent B, and reaction solution B have no particular meanings, which are only used to mark or distinguish the alkaline substance, solvent or reaction solution in different reaction steps, to avoid confusion.

The oxime ether acetate compound containing a phenylpyridine moiety in the present invention can be used for weeding in crops, the use is as follows: the oxime ether acetate compound containing a phenylpyridine moiety, as the active ingredient of a herbicide, is used for controlling and killing broadleaf weeds and grass weeds. The oxime ether acetate compound containing a phenylpyridine moiety in the present invention can be further prepared to preparations such as wettable powders, suspensions, creams, or water-dispersible granules, and the herbicidal activity of such compounds can be evaluated using the plate count method or potted plants live body test method. Results show that, the oxime ether acetate compound containing a phenylpyridine moiety is particularly suitable for the fields of crops such as corn and wheat, etc., and especially for inhibiting the growth of the weeds in the farmland such as mustard, *Beckmannia syzigachne*, chickweed, bluegrass, small *quinoa*, *Polypogon* grass, *Abutilon*, crabgrass, *Amaranthus retroflexus*, barnyard grass, *Eclipta*, dog point, etc.

Herbicidal activity assay results of the present invention show that: Compared with the clear water control, 30 days after postemergence spraying with compounds 19, 27, 83, 85, 98, 99, 101, 112, 120, 133 at a dose of 150 g a.i./ha, they exhibit inhibitory activity on the growth of broadleaf weeds such as mustard, small *quinoa, Abutilon, Amaranthus retroflexus* and *Eclipta prostrate*, but they almost have no activity on grass weeds such as crabgrass, dog point, etc.; in which compounds 101 and 103 exhibit inhibition rate up to 100% on the growth of broadleaf weeds such as mustard, small *quinoa, Abutilon, Amaranthus retroflexus* and *Eclipta prostrate*.

The results of screening tests for the herbicidal activity of compounds 101 and 133 show that, postemergence herbicide treatment is carried out at a dose of 150, 75, 37.5 g a.i./ha, and compounds 101 and 103 show an efficiency of 97.5~100% on the *amaranthus retroflexus* and *Eclipta prostrate*, and compound 133 shows an efficiency of 100% on the *Abutilon*, but showed not good activity or no activity on crabgrass, barnyard grass, dog point; when the pre-emergence soil treatment is carried out at a dose of 150 g a.i./ha, compounds 101 and 133 have good activity on broad-leaved weeds, but not good activity on grass weeds; when the dose is lowered, they showed significantly decreased activity or no activity on 6 kinds of weed targets.

Safety studies show that, it is safer for corns and barleys when compounds 101 and 133 are used in post-emergence spray treatment.

DETAILED DESCRIPTION OF THE EMBODIMENTS

Representative embodiments are detailed below, but they should not be understood as limiting the scope of the present invention.

The content of products below is measured by HPLC. The detection conditions are as follows:

Instruments: Shimadzu® LC-10AT; chromatographic column: Hypersil BDS $C_{18}$, 4.6 mm×150 mm, 5 μm; mobile phase: methanol/water=60:40; flow rate: 0.8 ml/min; detection wavelength: 254 nm; injection volume: 2 μL.

Example 1: Preparation of Compound 4 in Table 1

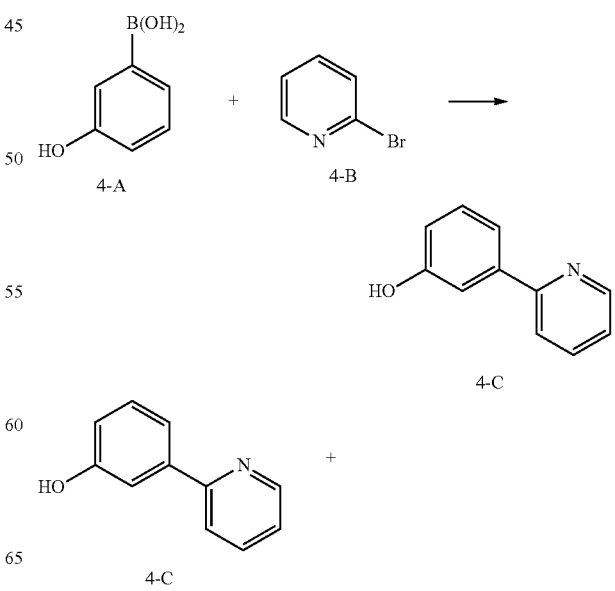

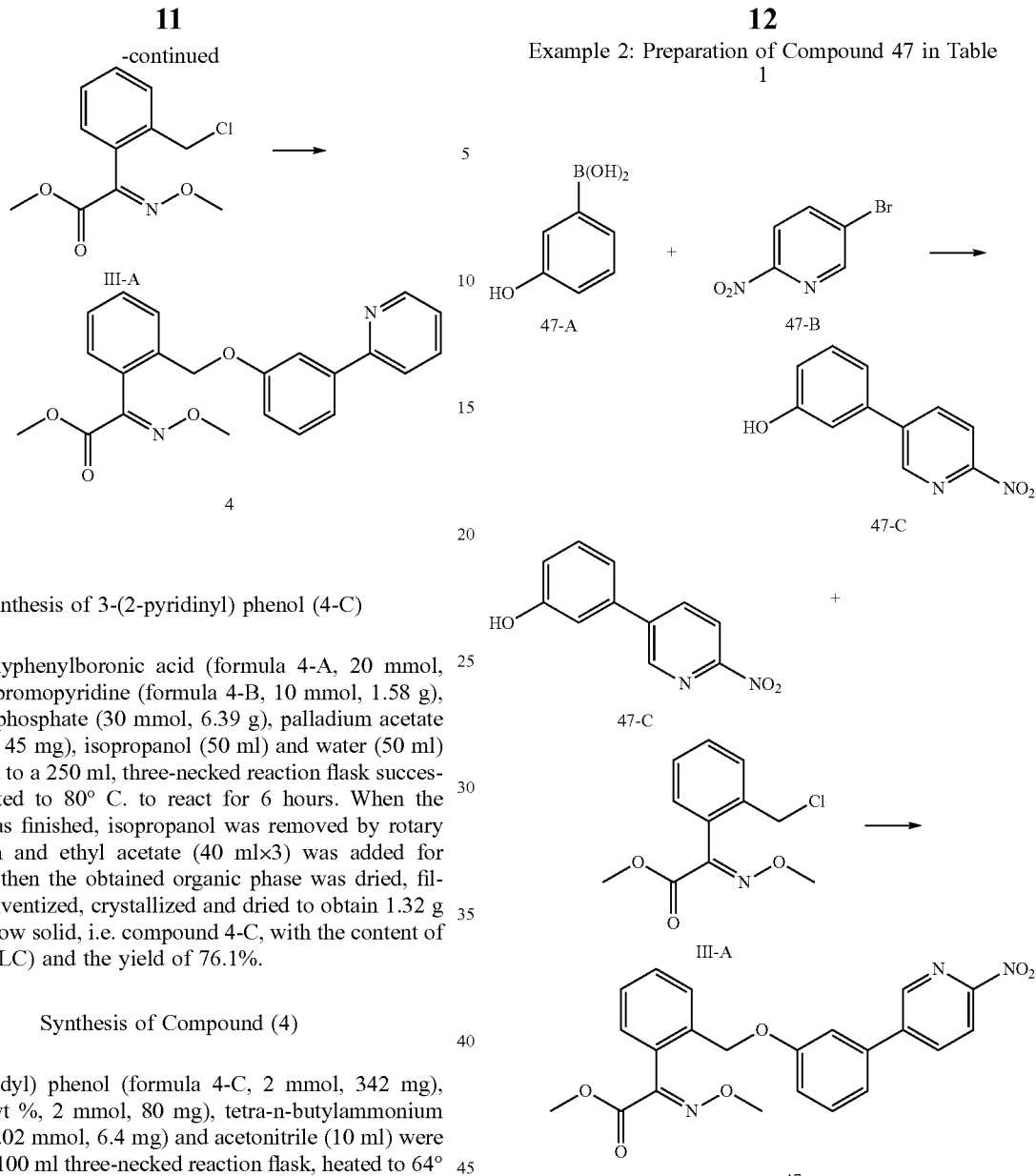

Synthesis of 3-(2-pyridinyl) phenol (4-C)

3-hydroxyphenylboronic acid (formula 4-A, 20 mmol, 2.77 g), 2-bromopyridine (formula 4-B, 10 mmol, 1.58 g), potassium phosphate (30 mmol, 6.39 g), palladium acetate (0.2 mmol, 45 mg), isopropanol (50 ml) and water (50 ml) were added to a 250 ml, three-necked reaction flask successively, heated to 80° C. to react for 6 hours. When the reaction was finished, isopropanol was removed by rotary evaporation and ethyl acetate (40 ml×3) was added for extraction, then the obtained organic phase was dried, filtered, desolventized, crystallized and dried to obtain 1.32 g of pale yellow solid, i.e. compound 4-C, with the content of 98.6% (HPLC) and the yield of 76.1%.

Synthesis of Compound (4)

3-(2-pyridyl) phenol (formula 4-C, 2 mmol, 342 mg), NaH (60 wt %, 2 mmol, 80 mg), tetra-n-butylammonium bromide (0.02 mmol, 6.4 mg) and acetonitrile (10 ml) were added to a 100 ml three-necked reaction flask, heated to 64° C. to stir for half an hour, and then (E)-2-(2'-chloro-methylphenyl)-2-carbonyl methyl acetate-O-methyl oxime (2.4 mmol, 580 mg) was added, heated to reflux temperature to react for 3-6 hours. When the reaction was finished, acetonitrile was removed by rotary evaporation, and ethyl acetate (30 ml×3) and water (30 ml) were added for extraction, the obtained organic phase was dried with anhydrous magnesium sulfate for 2 hours, then suction filtered and desolventized to obtain a crude product. The crude product was subjected to Silica gel column chromatography using the mixture of petroleum ether and acetone (V/V=10:1) as the mobile phase, and the eluent containing the target compound was collected, concentrated and dried to obtain 0.40 g of pale yellow oily liquid, i.e. the target compound 4, with the content of 96.5% (HPLC) and the yield of 51.7%.

$^1$H NMR (500 MHz, CDCl$_3$) δ 8.70 (m, 1H), 7.76 (td, J=7.7, 1.8 Hz, 1H), 7.71 (d, J=8.0 Hz, 1H), 7.61-7.57 (m, 3H), 7.49-7.34 (m, 3H), 7.26-7.23 (m, 2H), 6.96 (ddd, J=8.2, 2.6, 0.8 Hz, 1H), 5.06 (s, 2H), 4.04 (s, 3H); IR (KBr): ν$_{max}$ (cm$^{-1}$) 2943, 1729, 1586, 1456, 1300, 1212, 1069, 1018, 956, 771, 740, 693; MS (ESI): m/z (%)=377.20 [M+1].

Example 2: Preparation of Compound 47 in Table 1

Synthesis of 3-(2-nitro-5-pyridinyl) phenol (47-C)

3-hydroxyphenyl boronic acid (formula 47-A, 15 mmol, 2.08 g), 3-bromo-5-nitropyridine (formula 47-B, 10 mmol, 2.03 g), potassium phosphate (25 mmol, 5.33 g), palladium acetate (0.2 mmol, 45 mg), ethylene glycol (50 ml) and water (50 ml) were successively added to a 250 ml, three-necked reaction flask to react for 6 hours under the temperature of −10° C. When the reaction was finished, the solution was extracted with ethyl acetate (40 ml×3), then reversely extracted with saturated brine (40 ml×3), the organic phase was dried, filtered, desolventized, crystallized and dried to obtain 1.67 g of pale yellow solid, i.e. compound 47-C, with the content of 96.5% (HPLC) and the yield of 74.6%.

Synthesis of Compound (47)

3-(2-nitro-5-pyridinyl) phenol (formula 47-C, 2 mmol, 432 mg), NaH (60 wt %, 2.4 mmol, 96 mg), 18-crown-6 (0.1 mmol, 27 mg) and 10 ml DMF (10 ml) were added to a 100 ml three-necked reaction flask, stirred at −10° C. for half an hour, and then (E)-2-(2'-chloro-methylphenyl)-2-carbonyl methyl acetate-O-methyl oxime (2.4 mmol, 580 mg) was added to continue to react for 3-6 hours. When the reaction was finished, the solution was extracted with ethyl acetate (30 ml×3) and water (30 ml), and the combined organic phase was reversely extracted with saturated brine (30 ml×3), the organic phase was dried, suction filtered, and desolventized to obtain a crude product. The crude product was subjected to Silica gel column chromatography using the mixture of petroleum ether and acetone (V/V=15:1) as the mobile phase, and the eluent containing the target compound was collected, concentrated and dried to obtain 0.52 g of pale yellow solid, i.e. the target compound 47, with the content of 99.2% (HPLC) and the yield of 61.2%.

$^1$H NMR (500 MHz, CDCl$_3$) δ 8.38-8.34 (m, 2H), 7.59-7.54 (m, 2H), 7.50-7.49 (m, 1H), 7.39 (d, J=1.7 Hz, 1H), 7.33 (td, J=8.1, 2.4 Hz, 2H), 7.22 (s, 1H), 7.14-7.11 (m, 1H), 6.89 (ddd, J=8.2, 2.5, 0.9 Hz, 1H), 5.01 (s, 2H), 4.02 (s, 3H), 3.83 (s, 3H); MS (ESI): m/z (%)=421.96 [M+1].

Example 3: Preparation of Compound 48 in Table 1

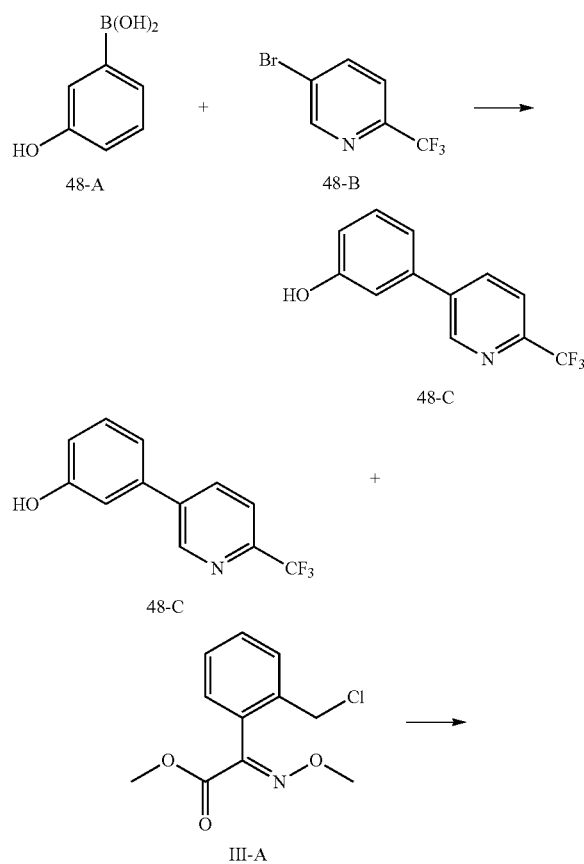

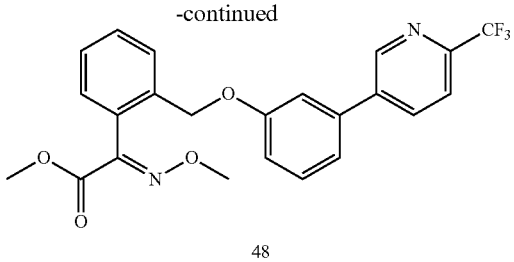

Synthesis of 3-(2-trifluoromethyl-5-pyridyl) phenol (Formula 48-C)

3-hydroxyphenyl boronic acid (formula 48-A, 12 mmol, 1.66 g), 2-bromo-5-trifluoromethyl-pyridine (formula 48-B, 10 mmol, 2.26 g), potassium phosphate (25 mmol, 5.33 g), palladium acetate (0.1 mmol, 23 mg), THF (50 ml) and water (50 ml) were successively added to a 250 ml, three-necked reaction flask, heated to reflux temperature to react for 6 hours. When the reaction was finished, THF was removed by rotary evaporation and ethyl acetate (40 ml×3) was added for extraction, dried, filtered, desolventized, crystallized and dried to obtain 2.10 g of pale yellow solid, i.e. compound of formula 48-C, with the content of 98.2% (HPLC) and the yield of 86.6%.

Synthesis of Compound (Formula 48)

3-(2-trifluoromethyl-5-pyridyl) phenol (formula 48-C, 2 mmol, 478 mg), NaOH (3 mmol, 120 mg), 18-crown-6 (0.2 mmol, 53 mg) and acetone (10 ml) were added to a 100 ml, three-necked reaction flask, heated to reflux temperature to react for half an hour, then (E)-2-(2'-chloro-methylphenyl)-2-carbonyl methyl acetate-O-methyl oxime (2.4 mmol, 580 mg) was added, cooled down to 60° C. to react for 3-6 hours. When the reaction was finished, acetonitrile was removed by rotary evaporation and ethyl acetate (30 ml×3) and water (30 ml) were added for extraction, the organic phase was dried, suction filtered, and desolventized to obtain a crude product. The crude product was subjected to Silica gel column chromatography using the mixture of petroleum ether and acetone (V/V=18:1) as the mobile phase, and the eluent containing the target compound was collected, concentrated and dried to obtain 0.58 g of pale yellow solid, i.e. the target compound 48, with the content of 98.8% (HPLC) and the yield of 64.5%.

$^1$H NMR (500 MHz, CDCl$_3$) δ 8.91 (s, 1H), 8.01 (d, J=8.0 Hz, 1H), 7.76 (d, J=8.1 Hz, 1H), 7.57 (d, J=7.4 Hz, 1H), 7.47 (td, J=7.5, 1.4 Hz, 1H), 7.43 (ddd, J=13.8, 9.1, 4.6 Hz, 2H), 7.24 (dd, J=7.5, 1.3 Hz, 1H), 7.19 (d, J=7.6 Hz, 1H), 7.11 (s, 1H), 7.00 (dd, J=8.3, 2.1 Hz, 1H), 5.05 (s, 2H), 4.03 (s, 3H), 3.84 (s, 3H); MS (ESI): m/z (%)=445.11 [M+1].

Example 4: Preparation of Compound 86 in Table 1

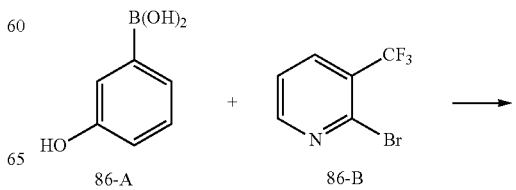

-continued

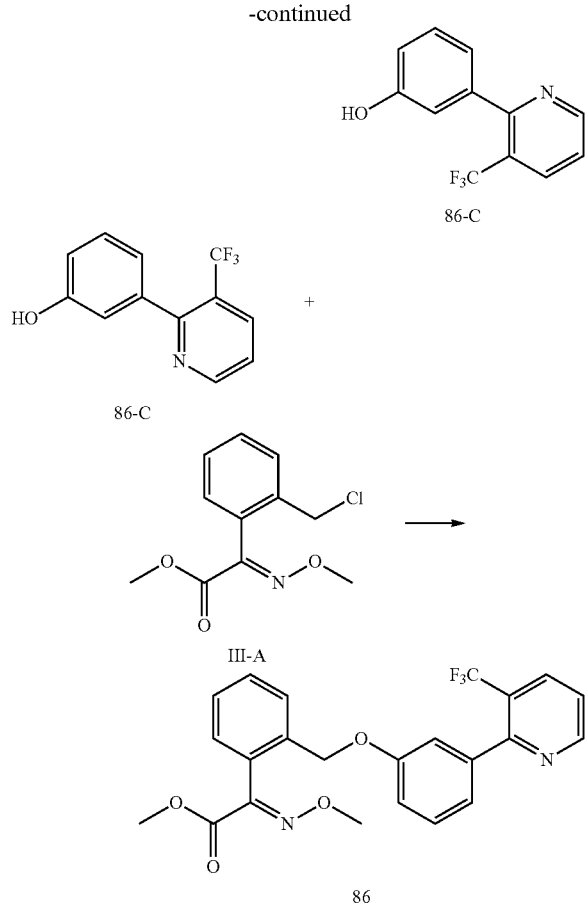

86

Synthesis of 3-(2-trifluoromethyl-5-pyridyl) phenol (Formula 86-C)

3-hydroxyphenyl boronic acid (formula 86-A, 12 mmol, 1.66 g), 2-bromo-5-trifluoromethyl-pyridine (formula 86-B, 10 mmol, 2.26 g), potassium carbonate (25 mmol, 3.45 g), palladium acetate (0.5 mmol, 110 mg), dioxane (50 ml) and water (50 ml) were successively added to a 250 ml, three-necked reaction flask, heated for reflux temperature to react for 6 hours. When the reaction was finished, dioxane was removed by rotary evaporation and ethyl acetate (40 ml×3) was added for extraction, the organic phase was dried, filtered, desolventized, crystallized and dried to obtain 1.94 g of pale yellow solid, i.e. compound of formula 86-C, with the content of 99.1% (HPLC) and the yield of 80.6%.

Synthesis of Compound (Formula 86)

3-(2-trifluoromethyl-5-pyridyl) phenol (formula 86-C, 2 mmol, 478 mg), K$_2$CO$_3$ (4 mmol, 552 mg), 18-crown-6 (0.2 mmol, 53 mg) and THF (10 ml) were added to a 100 ml, three-necked reaction flask, heated to reflux temperature to react for half an hour, and then (E)-2-(2'-chloro-methylphenyl)-2-carbonyl methyl acetate-O-methyl oxime (2.4 mmol, 580 mg) was added to continue the reaction at reflux temperature for 3-6 hours. When the reaction was finished, THF was removed by rotary evaporation and ethyl acetate (30 ml×3) and water (30 ml) were added for extraction, the organic phase was dried, suction filtered, desolventized to obtain a crude product. The crude product was subjected to Silica gel column chromatography using the mixture of petroleum ether and acetone (V/V=18:1) as the mobile phase, and the eluent containing the target compound was collected, concentrated and dried to obtain 0.48 g of pale yellow solid, i.e. the target compound 86, with the content of 99.1% (HPLC) and the yield of 53.7%.

$^1$H NMR (500 MHz, CDCl$_3$) δ 7.57 (s, 1H), 7.46 (d, J=1.3 Hz, 1H), 7.41 (d, J=1.1 Hz, 1H), 7.31 (s, 1H), 7.26-7.24 (m, 1H), 7.16 (s, 1H), 7.13 (s, 1H), 7.05 (s, 1H), 7.00 (d, J=1.9 Hz, 1H), 6.89 (dd, J=8.3, 2.3 Hz, 1H), 6.81 (dd, J=8.0, 2.4 Hz, 1H), 5.03 (s, 2H), 4.03 (s, 3H), 3.84 (s, 3H); MS (ESI): m/z (%)=445.17 [M+1].

Example 5: Preparation of Compound 87 in Table 1

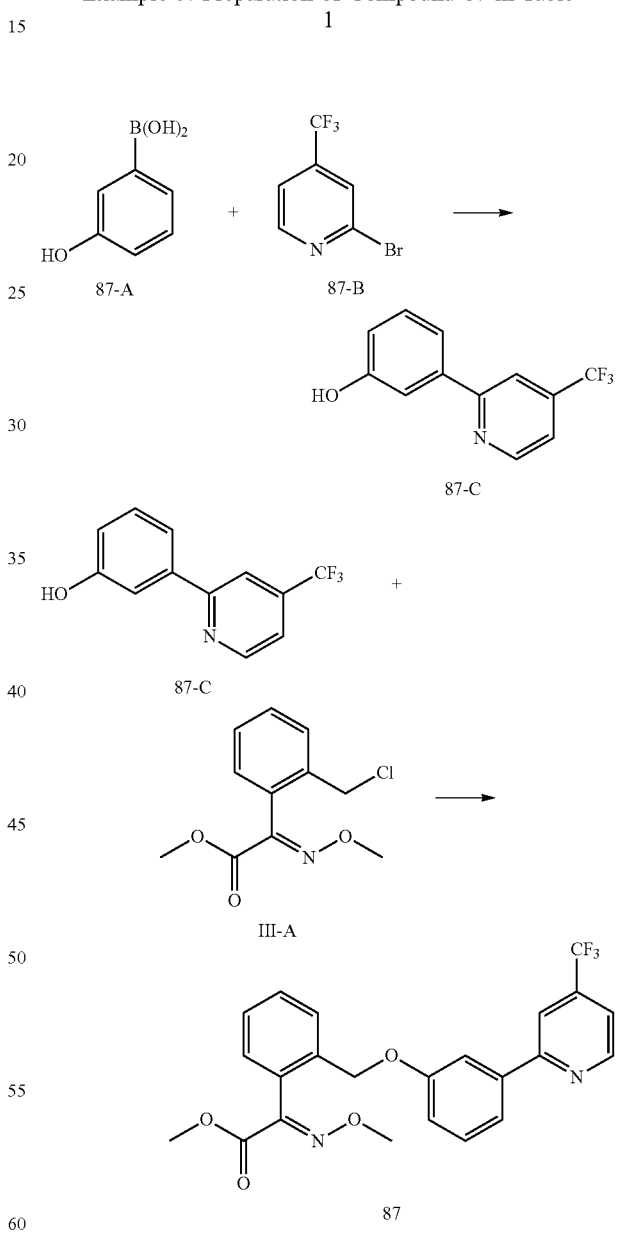

Synthesis of 3-(2-trifluoromethyl-5-pyridyl) phenol (Formula 87-C)

3-hydroxyphenyl boronic acid (formula 87-A, 12 mmol, 1.66 g), 2-bromo-5-trifluoromethyl-pyridine (formula 87-B, 10 mmol, 2.26 g), cesium fluoride (25 mmol, 3.80 g), palladium acetate (0.2 mmol, 45 mg), toluene (50 ml) were successively added to a 25 ml, three-necked reaction flask to react at room temperature (25° C.) for 6 hours. When the reaction was finished, the solution was extracted with ethyl acetate (40 ml×3) and water (40 ml), the organic phase was dried, filtered, desolventized, crystallized and dried to obtain 2.09 g of pale yellow solid, i.e. compound of formula 87-C, with the content of 97.8% (HPLC) and the yield of 85.5%.

Synthesis of Compound (87)

3-(2-trifluoromethyl-5-pyridyl) phenol (formula 87-C, 2 mmol, 478 mg), NaH (60 wt %, 3 mmol, 120 mg), 18-crown-6 (0.05 mmol, 13 mg) and N'N-dimethylacetamide (10 ml) were added to a 100 ml, three-necked reaction flask, stirred to react at −10° C. for half an hour, and then (E)-2-(2'-chloro-methylphenyl)-2-carbonyl methyl acetate-O-methyl oxime (2.4 mmol, 580 mg) was added to continue the reaction for 3-6 hours at −10° C. When the reaction was finished, the solution was extracted with ethyl acetate (30 ml×3) and water (30 ml), and the combined organic phase was reversely extracted by saturated brine (30 ml×3), dried, suction filtered, and desolventized to obtain a crude product. The crude product was subjected to Silica gel column chromatography using the mixture of petroleum ether and acetone (V/V=18:1) as the mobile phase, and the eluent containing the target compound was collected, concentrated and dried to obtain 0.64 g of pale yellow solid, i.e. the target compound 87, with the content of 99.5% (HPLC) and the yield of 71.2%.

$^1$H NMR (500 MHz, CDCl$_3$) δ 8.92 (d, J=5.2 Hz, 1H), 7.97 (s, 1H), 7.69-7.53 (m, 4H), 7.48-7.39 (m, 3H), 7.23 (dd, J=7.5, 1.3 Hz, 1H), 7.07-6.99 (m, 1H), 5.10 (s, 2H), 4.04 (s, 3H), 3.86 (s, 3H); MS (ESI): m/z (%)=445.12 [M+1].

Example 6: Preparation of Compound 101 in Table 1

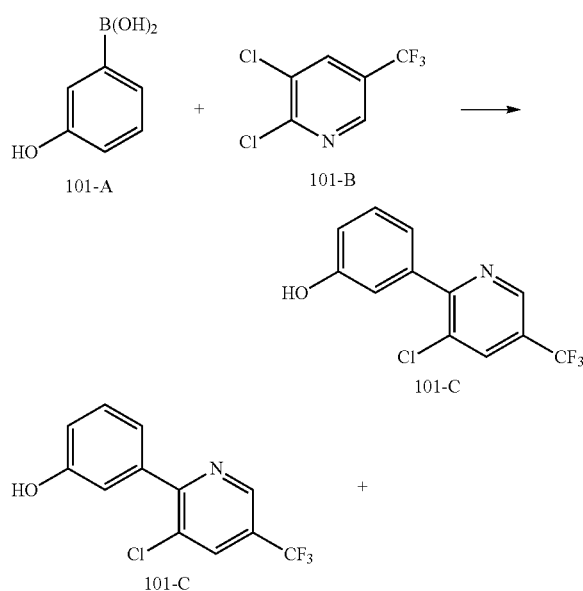

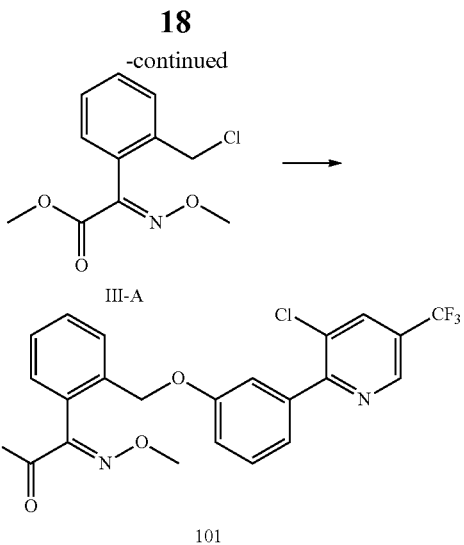

Synthesis of 3-(2-trifluoromethyl-5-pyridyl) phenol (Formula 101-C)

3-hydroxyphenyl boronic acid (formula 101-A, 10 mmol, 1.38 g), 2-bromo-5-trifluoromethylpyridine (formula 101-B, 10 mmol, 2.26 g), cesium fluoride (20 mmol, 3.04 g), palladium acetate (0.2 mmol, 45 mg), xylene (50 ml) were successively added to a 250 ml, three-necked reaction flask to react at room temperature (25° C.) for 6 hours. When the reaction was finished, the solution was extracted with ethyl acetate (40 ml×3) and water (40 ml), dried, filtered, desolventized, crystallized and dried to obtain 2.09 g of pale yellow solid, i.e. compound of formula 101-C, with the content of 97.8% (HPLC) and the yield of 85.5%.

Synthesis of Compound (101)

3-(2-trifluoromethyl-5-pyridyl) phenol (formula 101-C, 2 mmol, 478 mg), NaH (60 wt %, 3 mmol, 120 mg), 18-crown-6 (0.2 mmol, 53 mg) and CH$_2$Cl$_2$ (10 ml) were added to a 100 ml, three-necked reaction flask, stirred to react at −10° C. for half an hour, and then (E)-2-(2'-chloromethylphenyl)-2-carbonyl methyl acetate-O-methyl oxime (2.4 mmol, 580 mg) was added to continue to react for 3-6 hours at −10° C. When the reaction was finished, the solution was extracted with ethyl acetate (30 ml×3) and water (30 ml), and the combined organic phase was reversely extracted with saturated brine (30 ml×3), dried, suction filtered, and desolventized to obtain a crude product. The crude product was subjected to Silica gel column chromatography using the mixture of petroleum ether and acetone (V/V=18:1) as the mobile phase, and the eluent containing the target compound was collected, concentrated and dried to obtain 0.64 g of pale yellow solid, i.e. the target compound 101, with the content of 99.5% (HPLC) and the yield of 71.2%.

$^1$H NMR (500 MHz, CDCl$_3$) δ 8.85 (d, J=1.1 Hz, 2H), 8.05 (d, J=1.5 Hz, 2H), 7.58 (d, J=7.5 Hz, 2H), 7.46 (dd, J=7.6, 1.4 Hz, 2H), 7.44-7.37 (m, 4H), 7.36 (dd, J=5.1, 3.9 Hz, 2H), 7.31-7.28 (m, 3H), 7.23 (dd, J=7.5, 1.2 Hz, 2H), 7.03 (ddd, J=8.2, 2.6, 1.0 Hz, 2H), 5.03 (s, 4H), 4.02 (s, 6H), 3.84 (s, 6H); MS (ESI): m/z (%)=478.87 [M+1].

Example 7: Preparation of Compound 133 in Table 1

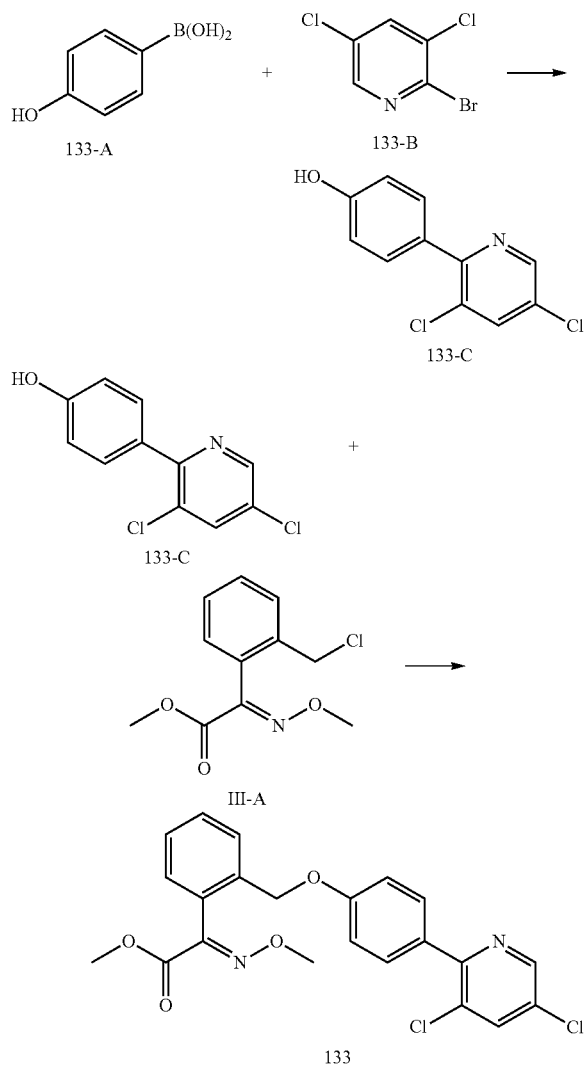

Synthesis of 3-(2-trifluoromethyl-5-pyridyl) phenol (133-C)

3-hydroxyphenyl boronic acid (133-A, 12 mmol, 1.66 g), 2-bromo-5-trifluoromethylpyridine (133-B, 10 mmol, 2.26 g), cesium fluoride (25 mmol, 3.80 g), palladium acetate (0.2 mmol, 45 mg), PEG2000 (50 ml) were successively added to a 250 ml, three-necked reaction flask to react at room temperature (25° C.) for 6 hours. When the reaction was finished, the solution was extracted with ethyl acetate (40 ml×3) and water (40 ml), the organic phase was dried, filtered, desolventized, crystallized and dried to obtain 2.09 g of pale yellow solid, i.e. compound 133-C, with the content of 97.8% (HPLC) and the yield of 85.5%.

Synthesis of Compound (133)

3-(2-trifluoromethyl-5-pyridyl) phenol (133-C, 2 mmol, 478 mg), NaH (60 wt %, 3 mmol, 120 mg), 18-crown-6 (0.2 mmol, 53 mg) and DMSO (10 ml) were added to a 100 ml, three-necked reaction flask, stirred to react at −10° C. for half an hour, and then (E)-2-(2'-chloro-methylphenyl)-2-carbonyl methyl acetate-O-methyl oxime (2.4 mmol, 580 mg) was added to continue to react for 3-6 hours at −10° C. When the reaction was finished, the solution was extracted with ethyl acetate (30 ml×3) and water (30 ml), and the combined organic phase was reversely extracted with saturated brine (30 ml×3), dried, suction filtered, and desolventized to obtain a crude product. The crude product was subjected to Silica gel column chromatography using the mixture of petroleum ether and acetone (V/V=18:1) as the mobile phase, and the eluent containing the target compound was collected, concentrated and dried to obtain 0.64 g of pale yellow solid, i.e. the target compound 133, with the content of 99.5% (HPLC) and the yield of 71.2%.

$^1$H NMR (500 MHz, CDCl$_3$) δ 8.54 (d, J=2.2 Hz, 1H), 7.83 (d, J=2.2 Hz, 1H), 7.72-7.66 (m, 2H), 7.61-7.53 (m, 1H), 7.47-7.39 (m, 2H), 7.24 (dd, J=7.5, 1.3 Hz, 1H), 7.02-6.97 (m, 2H), 5.03 (s, 2H), 4.05 (s, 3H), 3.86 (s, 3H); MS (ESI): m/z (%)=444.88 [M+1].

Examples 8-10 are examples of Preparations

The following content of ingredients are calculated by mass percentages. All active ingredients are selected from compounds in Table 1.

Example 8: 60% Wettable Powder

TABLE 2

| List of ingredients of 60% wettable powder | |
|---|---|
| Ingredient | Content |
| Compound 48 | 60% |
| SDBS | 1% |
| sodium lignosulphonate | 6% |
| Diffusant NNO | 5% |
| Diatomite | 28% |

All ingredients were mixed uniformly and smashed in a pulverizer until the fineness reaches the standard (≤44 μm), to obtain a wettable powder containing an active ingredient (i.e. compound 48), whose content was 60%.

Example 9: 35% Emulsifiable Concentrate (EC)

TABLE 3

| List of ingredients of 35% EC | |
|---|---|
| Ingredient | Content |
| Compound 48 | 35% |
| Cyclohexanone | 20% |
| Emulsifier OP-10 (emulsifier A) | 7% |
| SDBS (emulsifier B) | 5% |
| Solvent oil | 33% |

Compound 48 was dissolved in cyclohexanone and solvent oil and then emulsifier A and emulsifier B were added to mix uniformly to obtain a transparent homogeneous solution, i.e. 35% emulsifiable concentrate containing an active ingredient (i.e. Compound 48).

Example 10: 50% Water Dispersible Granules

TABLE 4

| 50% water dispersible granules | |
|---|---|
| Ingredient | Content |
| Compound 48 | 50% |
| Sorbitan sulfate | 1% |
| Polyvinylpyrrolidone | 3% |
| sodium lignosulfonate | 10% |
| Diatomite | 36% |

The above ingredients were mixed uniformly and ground, then a small amount of water was added, kneaded, granulated and dried, to obtain 50% water dispersible granules containing active ingredient (Compound 48).

Example 11: Determination of Herbicidal Activity

Preparation

The raw drug which was selected from the compounds in table 1 was weighed using an analytical balance (0.0001 g), and dissolved in DMF containing 1 wt % Tween-80 emulsifier to prepare a mother liquor of raw drug with a mass concentration of 1.0~5.0%, and then diluted with distilled water, to prepare preparations at desired concentrations according to the ratio of ingredients in Examples 8, 9 and 10.

Test Method

Culture dish method (general screening): The test targets were radish, cucumber, rape, wheat, sorghum and barnyard grass; the seeds of wheat, sorghum and radish were germinated in advance, and the uniform emerge-germinating seeds were used in the test. The above targets were placed in culture dishes with a diameter of 9 cm paved with double filter paper respectively, and added 9 mL of a solution of a new compound at concentration of 100 mg/L to each culture dish; after uniformly immersed, they were numbered and labeled, cultured in an artificial climate chamber, wherein the temperature was set at 28° C., the illumination light intensity was set at 3000 Lux, the photoperiod was 16 h light/8 h dark, and RH was 75%; 7 days later, the growth inhibition rate (%) of roots and stems of the targets were observed and calculated.

Potted Plants Live Body Test Method (Determination of High-Activity Compounds):

The test targets were mustard, small *quinoa, Abutilon, amaranthus retroflexus, Eclipta prostrata*, crabgrass, dog point. A pot with a diameter of 7.5 cm was used, filled with composite soil (garden soil:nursery matrix, 1:2, v/v) to ¾ of the pot, then the above six kinds of weeds targets were directly seeded (germination rate ≥85%), covered with soil at a thickness of 0.2 cm. When the weeds grew to 3-leaf stage, pre-emergence soil treatment for weeds planting, and then spraying was performed. After administration of all compounds in the automatic spray tower (Model: 3WPSH-700E) at the dose of 150, 75, 37.5 g a.i./ha, they were cultured in greenhouse culture when the foliage liquid was dried, 30 days later, the comprehensive inhibition rate on the weeds was observed and calculated (%).

Test Results

TABLE 8

Test results of culture dish test for herbicidal activity of some compounds (inhibition rate/%, 100 mg/L)

| Compound No. | Wheat | | Chinese sorghum | | Barnyardgrass | | Cucumber | | Rape | | Radish | |
|---|---|---|---|---|---|---|---|---|---|---|---|---|
| | Root | Stem | Root | Stem | Root | Stem | Root | Stem | Root | Stem | Root | Stem |
| 4 | 0 | 0 | 0 | 0 | 30 | 30 | 30 | 0 | 30 | 0 | 50 | 30 |
| 7 | 20 | 0 | 0 | 0 | 50 | 20 | 30 | 0 | 60 | 30 | 20 | 0 |
| 19 | 30 | 0 | 80 | 30 | 70 | 30 | 90 | 70 | 100 | 100 | 80 | 80 |
| 27 | 50 | 0 | 50 | 0 | 60 | 30 | 60 | 0 | 50 | 50 | 50 | 20 |
| 32 | 0 | 0 | 0 | 0 | 0 | 0 | 0 | 0 | 80 | 80 | 80 | 50 |
| 67 | 30 | 0 | 50 | 50 | 50 | 0 | 50 | 0 | 50 | 30 | 50 | 50 |
| 75 | 0 | 0 | 0 | 0 | 30 | 30 | 30 | 0 | 0 | 0 | 0 | 0 |
| 83 | 60 | 20 | 80 | 30 | 80 | 0 | 80 | 30 | 80 | 50 | 50 | 50 |
| 84 | 0 | 0 | 0 | 0 | 80 | 0 | 30 | 0 | 50 | 0 | 0 | 0 |
| 85 | 60 | 20 | 80 | 30 | 80 | 0 | 80 | 30 | 80 | 50 | 50 | 50 |
| 98 | 20 | 0 | 50 | 30 | 60 | 20 | 50 | 80 | 50 | 80 | 50 | 80 |
| 99 | 30 | 0 | 50 | 50 | 50 | 0 | 70 | 0 | 60 | 30 | 60 | 50 |
| 101 | 50 | 20 | 100 | 100 | 100 | 95 | 95 | 100 | 100 | 100 | 100 | 100 |
| 104 | 0 | 0 | 0 | 0 | 0 | 0 | 20 | 0 | 50 | 0 | 0 | 0 |
| 110 | 0 | 0 | 0 | 0 | 0 | 0 | 20 | 0 | 20 | 0 | 0 | 0 |
| 112 | 0 | 0 | 0 | 0 | 0 | 0 | 50 | 80 | 50 | 80 | 50 | 80 |
| 120 | 20 | 0 | 50 | 30 | 60 | 20 | 70 | 30 | 60 | 0 | 50 | 0 |
| 133 | 50 | 0 | 100 | 100 | 100 | 100 | 100 | 100 | 100 | 100 | 100 | 100 |
| Pyribambenz isopropyl | 95 | 95 | 100 | 90 | 100 | 95 | 95 | 90 | 100 | 100 | 100 | 90 |

The results of dish test for herbicidal activity showed (table 8) that, compounds 19, 27, 83, 85, 98, 99, 101, 112, 120, 133 exhibited strong growth inhibition on the roots/stems of 3 or more test targets (≥60%) at a dose of 100 mg/L, and then potted plants live body test method was carried out for the above 10 compounds to further identify their herbicidal activity.

TABLE 9

General screening test results of herbicidal activity for some compounds
(efficiency/%, 150 g a.i./ha)

| Compound No. | Mustard | Small quinoa | Abutilon | amaranthus retroflexus | Eclipta prostrata | Crabgrass | Dog point |
|---|---|---|---|---|---|---|---|
| Postemergence spraying | | | | | | | |
| 19 | 50 | 60 | 40 | 50 | 50 | 0 | 0 |
| 27 | 80 | 60 | 60 | 80 | 80 | 0 | 0 |
| 83 | 0 | 50 | 30 | 20 | 0 | 0 | 0 |
| 85 | 30 | 0 | 50 | 0 | 50 | 0 | 0 |
| 98 | 100 | 75 | 80 | 80 | 80 | 0 | 0 |
| 99 | 60 | 50 | 20 | 40 | 25 | 0 | 0 |
| 101 | 100 | 100 | 100 | 100 | 100 | 0 | 0 |
| 112 | 100 | 75 | 50 | 80 | 60 | 0 | 0 |
| 120 | 40 | 60 | 50 | 20 | 30 | 0 | 0 |
| 133 | 100 | 100 | 100 | 100 | 100 | 0 | 0 |
| Clear water | 0 | 0 | 0 | 0 | 0 | 0 | 0 |
| Pre-emergence soil treatment | | | | | | | |
| 19 | 0 | 25 | 0 | 30 | 0 | 0 | 0 |
| 27 | 30 | 25 | 0 | 50 | 0 | 0 | 0 |
| 83 | 0 | 30 | 0 | 20 | 0 | 0 | 0 |
| 85 | 20 | 0 | 20 | 0 | 0 | 0 | 0 |
| 98 | 50 | 45 | 60 | 50 | 50 | 0 | 0 |
| 99 | 0 | 30 | 0 | 0 | 0 | 0 | 0 |
| 101 | 100 | 100 | 100 | 100 | 85 | 80 | 50 |
| 112 | 50 | 45 | 0 | 50 | 0 | 0 | 0 |
| 120 | 20 | 50 | 0 | 0 | 0 | 0 | 0 |
| 133 | 100 | 100 | 100 | 100 | 100 | 50 | 50 |
| Clear water | 0 | 0 | 0 | 0 | 0 | 0 | 0 |

Potted plants live body test results (Table 9) showed that, compared with the clear water control, 30 days after administration at the dose of 150 g a.i./ha, compounds 19, 27, 83, 85, 98, 99, 101, 112, 120, 133 exhibited herbicidal activity on broadleaf weeds targets such as mustard, small *quinoa*, *Abutilon*, *amaranthus retroflexus* and *Eclipta prostrate*, but poor activity for the grass targets such as crabgrass and dog point. Generally, the activity of the compounds used in postemergence spray treatment is superior to that of the compounds used in pre-emergence soil treatment. Compounds 101 and 133 exhibited 100% inhibition rate on the growths of broadleaf weeds such as mustard, small *quinoa*, *Abutilon, Amaranthus retroflexus* and *Eclipta prostrate* at the dose of 150 g a.i./ha. Therefore, further screening of herbicidal activity of the two compounds was performed.

TABLE 10

Results of screening of herbicidal activity of compounds 101 and 133
(efficiency/%)

| Compound No. | Dose g a.i./ha | Abutilon | crabgrass | amaranthus retroflexus | Barnyardgrass | Eclipta prostrate | Dog point |
|---|---|---|---|---|---|---|---|
| postemergence spraying | | | | | | | |
| 101 | 150 | 100 | 0 | 100 | 0 | 100 | 0 |
|  | 75 | 60 | 0 | 100 | 0 | 100 | 0 |
|  | 37.5 | 30 | 0 | 100 | 0 | 97.5 | 0 |
| 133 | 150 | 100 | 0 | 100 | 0 | 100 | 0 |
|  | 75 | 100 | 0 | 100 | 0 | 100 | 0 |
|  | 37.5 | 100 | 0 | 100 | 0 | 97.5 | 0 |
| Pyribambenz isopropyl | 150 | 0 | 50 | 70 | 50 | 0 | 80 |
| Pre-emergence soil treatment | | | | | | | |
| 101 | 150 | 100 | 80 | 100 | 0 | 85 | 50 |
|  | 75 | 0 | 0 | 15 | 0 | 0 | 0 |
|  | 37.5 | 0 | 0 | 0 | 0 | 0 | 0 |
| 133 | 150 | 100 | 50 | 100 | 0 | 100 | 50 |
|  | 75 | 0 | 0 | 30 | 0 | 0 | 0 |
|  | 37.5 | 0 | 0 | 20 | 0 | 0 | 0 |
| pre-emergence soil treatment | 150 | 100 | 97.5 | 95 | 97.5 | 75 | 97.5 |

The results of preliminary screening tests for herbicidal activity of compounds 101 and 133 showed that (table 10), compounds 101 and 103 were used in postemergence herbicidal treatment at a dose of 150, 75, 37.5 g a.i./ha and showed an efficiency of 97.5~100% on the *amaranthus retroflexus* and *Eclipta prostrate*, and compound 133 showed an efficiency of 100% on the *Abutilon*, but showed not good activity or no activity on crabgrass, barnyard grass, dog point; when they were used in pre-emergence soil treatment at a dose of 150 g a.i./ha, compounds 101 and 133 had better activity on broad-leaved weeds, but not good activity on the grass weeds; when the dose was lowered, they showed significantly decreased activity or no activity on 6 kinds of weed targets.

TABLE 11

Crop inhibition rate of compounds 101 and 133 (%)

| Compound No. | Dose g a.i./ha | Corn | Soybean | Cotton | Rice | Rape | Barley |
|---|---|---|---|---|---|---|---|
| 101 | 150 | 0 | 40 | 50 | 30 | 50 | 0 |
| 133 | 150 | 0 | 40 | 50 | 30 | 100 | 0 |

The safety test showed (table 11) that, it was safer for corns and barleys when compounds 101 and 133 were used in post-emergence spray treatment.

The invention claimed is:

1. An oxime ether acetate compound containing a phenylpyridine moiety, having formula (I):

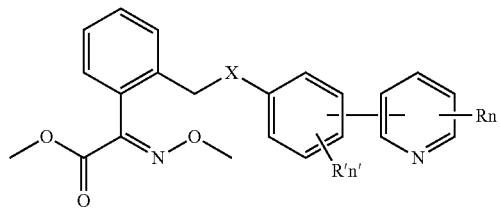

(I)

wherein, X is O, S, COO or NH;

R and n represent a substituent on the pyridine ring and the number of substituents respectively, wherein $0 \leq n \leq 4$ and n is a natural number, when n=0, it means that the pyridine ring does not contain R, when $0 < n \leq 4$, each of the substituents on the pyridine ring (i.e. R) is selected from the group consisting of $CH_3$, $OCH_3$, Br, Cl, F, CN, $CF_3$, $NO_2$ and OH, and the substituents on the pyridine ring are same or different;

R' and n' represent a substituent on the benzene ring and the number of substituents, wherein $0 \leq n' \leq 4$ and n' is a natural number, when n'=0, it means that the benzene ring does not contain R', when $0 < n' \leq 4$, each of the substituents on the pyridine ring independent from each other is selected from the group consisting of $CH_3$, $OCH_3$, Br, Cl, F, CN, $CF_3$, $NO_2$ and OH, and the substituents on the benzene ring are same or different;

relative to the benzene ring, pyridinyl is positioned at ortho-, meta- or para-position of X on the benzene ring, and relative to the pyridine ring, the substituted phenyl is positioned at ortho-, meta- or para-position of N on the pyridine ring.

2. The oxime ether acetate compound according to claim 1 having one of formulae (I-1)~(I-9),

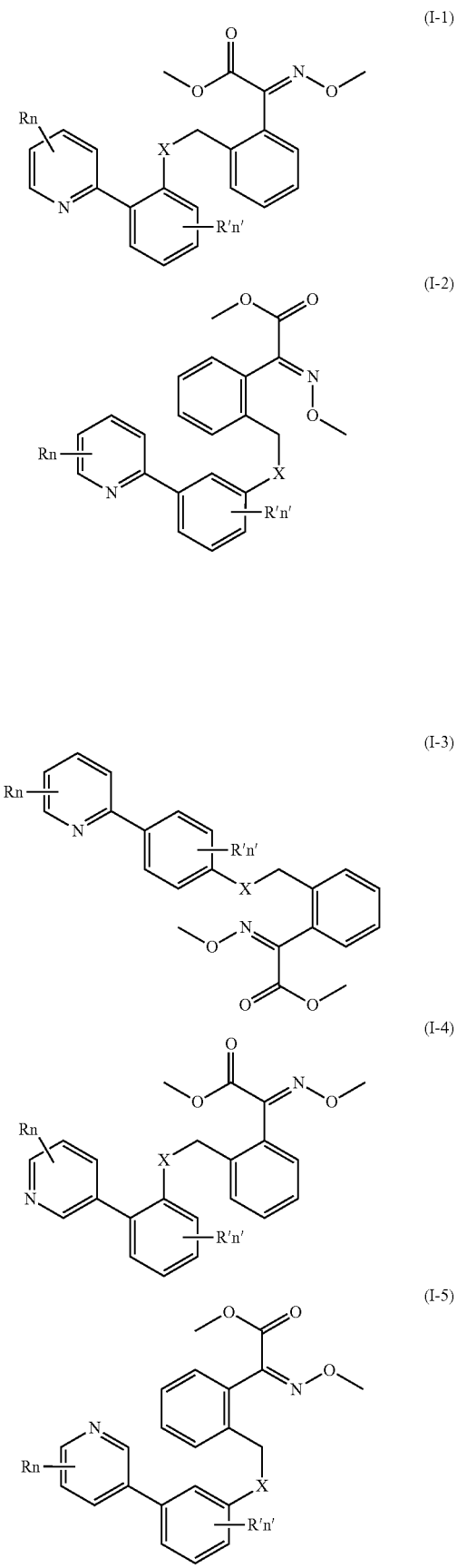

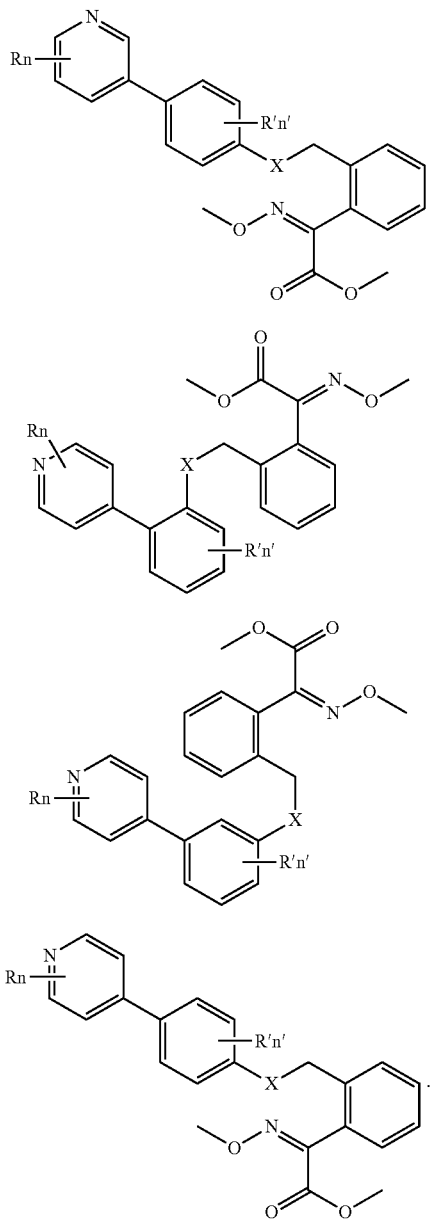

3. The oxime ether acetate compound according to claim 1, wherein X is O.

4. The oxime ether acetate compound according to claim 3, wherein R on the pyridine ring is selected from the group consisting of Br, Cl, F, CN, $CF_3$ and $NO_2$; when $0<n\leq4$, the substituents on the pyridine ring are same;

R' on the benzene ring is selected from the group consisting of Br, Cl, F, CN, $CF_3$ and $NO_2$, when $0<n'\leq4$, the substituents on the benzene ring are same; and relative to the pyridine ring, the substituted phenyl group is positioned at ortho-, meta- or para-position of N on the pyridine ring, and relative to the benzene ring, the pyridinyl group is positioned at meta-position of X on the benzene ring.

5. The oxime ether acetate compound according to claim 3, wherein relative to the pyridine ring, the substituted phenyl group is positioned at ortho-position of N on the pyridine ring.

6. A method for preparing the oxime ether acetate compound containing a phenylpyridine moiety according to claim 1, comprising the following steps:

(1) preparation of a compound of formula (II): mixing a compound of formula (IV), a compound of formula (V), an alkaline substance A, a palladium catalyst and a solvent A; subjecting the mixture to a reaction at the temperature ranging from −10° C. to the reflux temperature for 0.5-20 hours to obtain a reaction solution A; post-treating the solution A to obtain a compound of formula (II); in which the alkaline substance A is selected from the group consisting of potassium carbonate, potassium phosphate, potassium hydroxide, potassium t-butoxide and cesium fluoride; the palladium catalyst is selected from the group consisting of palladium chloride, palladium acetate, tetrakis (triphenyl phosphine) palladium, palladium triphenylphosphine acetate and [1,1'-bis (diphenylphosphino) ferrocene] dichloropalladium; the solvent A is selected from the group consisting of isopropyl alcohol, ethylene glycol, glycerol, ethanol, water, tetrahydrofuran, dioxane, toluene, xylene, PEG2000, and any combination thereof;

(2) preparation of the compound of formula (I): mixing the compound of formula (II) obtained in step (1), an alkaline substance B, a phase transfer catalyst and a solvent B; subjecting the mixture to a reaction at the temperature ranging from −10° C. to the reflux temperature for 0.1-2 hours; then adding a compound of formula (III), continuing to react at the temperature ranging from −10° C. to the reflux temperature for 0.5-20 hours to obtain a reaction solution B; and post-treating the solution B to obtain the compound of formula (I); in which, the alkaline substance B is selected from the group consisting of sodium hydride, sodium methoxide, tert-butyllithium, sodium hydroxide, potassium hydroxide, potassium carbonate and sodium carbonate; the phase transfer catalyst is selected from the group consisting of n-butyl ammonium bromide and 18-crown-6; and the solvent B is selected from the group consisting of N, N-dimethylformamide, N, N-dimethylacetamide, tetrahydrofuran, acetonitrile, acetone, methylene chloride, dimethyl sulfoxide, and any combination thereof;

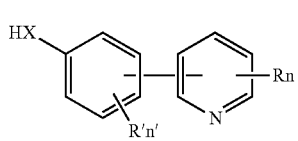

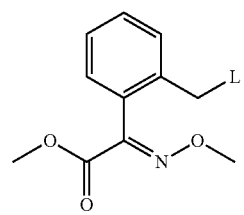

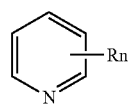

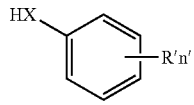

in the formula (III), L represents a leaving group and is Cl or Br, in the formula (II), (IV) or (V), R, n, R', and n' are as defined in claim 1, in the formula (II) or (V), X is as defined in claim 1, in the formula (II), relative to the benzene ring, pyridinyl is positioned at ortho-, meta- or para-position of XH on the benzene ring, and relative to the pyridine ring, the substituted phenyl is positioned at ortho-, meta- or para-position of N on the pyridine ring.

7. The method according to claim 6, wherein in step (1), the mole ratio of the compound of formula (IV) to the compound of formula (V) ranges from 1:1 to 1:2, the mole ratio of the compound of formula (IV) to the alkaline substance A ranges from 1:2 to 1:3, the mole ratio of the compound of formula (IV) to the palladium catalyst ranges from 1:0.01 to 1:0.2; and the ration of the solvent A to the compound of formula (IV) ranges from 20 mL/g to 70 mL/g.

8. The method according to claim 6, wherein in step (2), the mole ratio of the compound of formula (II) to the compound of formula (III) ranges from 1:1 to 1:2, the mole ratio of the compound of formula (II) to the alkaline substance B ranges from 1:1 to 1:3, the mole ratio of the compound of formula (II) to the phase transfer catalyst ranges from 1:0.01 to 1:0.2; and the ratio of the solvent B to the compound of formula (II) ranges from 20 mL/g to 30 mL/g.

9. A method of using the oxime ether acetate compound containing a phenylpyridine moiety according to claim 1 for controlling and killing broadleaf weeds or grass weeds, comprising applying to the broadleaf weeds or grass weeds a herbicide in which the oxime ether acetate compound is used as an active ingredient.

10. The method according to claim 9, wherein the oxime ether acetate compound containing a phenylpyridine moiety is prepared into wettable powders, suspensions, emulsifiable concentrates or water-dispersible granules, and used for controlling and killing mustard, *Beckmannia syzigachne*, chickweed, bluegrass, small *quinoa, Polypogon* grass, *abutilon*, crabgrass, *Amaranthus retroflexus*, barnyard grass, *Eclipta*, and dog point.

11. An oxime acetate compound according to claim 1 wherein the n represents 0≤n≤3 and n' represents 0≤n'≤3.

* * * * *